United States Patent
Lim et al.

(10) Patent No.: US 12,285,754 B2
(45) Date of Patent: Apr. 29, 2025

(54) DEVICES AND METHODS FOR HIGH-THROUGHPUT SCREENING OF CHEMICAL AND BIOCHEMICAL COMPOUNDS

(71) Applicant: ImpriMed, Inc., Palo Alto, CA (US)

(72) Inventors: Sungwon Lim, Palo Alto, CA (US); Jun Kim, Mountain View, CA (US); Jamin Koo, Seoul (KR); Hye-Ryeon Lee, Palo Alto, CA (US)

(73) Assignee: ImpriMed, Inc., Palo Alto, CA (US)

( * ) Notice: Subject to any disclaimer, the term of this patent is extended or adjusted under 35 U.S.C. 154(b) by 935 days.

(21) Appl. No.: 16/744,005

(22) Filed: Jan. 15, 2020

(65) Prior Publication Data
US 2020/0147606 A1 May 14, 2020

Related U.S. Application Data

(63) Continuation of application No. PCT/US2018/044306, filed on Jul. 30, 2018.
(Continued)

(51) Int. Cl.
*B01L 3/00* (2006.01)
*G01N 33/487* (2006.01)
(Continued)

(52) U.S. Cl.
CPC ......... *B01L 3/5023* (2013.01); *B01L 3/50855* (2013.01); *G01N 33/48778* (2013.01);
(Continued)

(58) Field of Classification Search
CPC .... B01L 3/5023; B01L 3/5025; B01L 3/5027; B01L 2300/069; B01L 2300/0819;
(Continued)

(56) References Cited

U.S. PATENT DOCUMENTS

| | | | | |
|---|---|---|---|---|
| 4,071,315 A | * | 1/1978 | Chateau | B01L 3/545 436/805 |
| 5,972,694 A | | 10/1999 | Mathus | |

(Continued)

FOREIGN PATENT DOCUMENTS

| | | |
|---|---|---|
| CN | 103217518 A | 7/2013 |
| JP | 2003083964 A | 3/2003 |

(Continued)

OTHER PUBLICATIONS

Imprimed Inc., International Preliminary Report on Patentability, PCT/US2018/044306, Oct. 10, 2018, 6 pages.
(Continued)

*Primary Examiner* — Jill A Warden
*Assistant Examiner* — Dwayne K Handy
(74) *Attorney, Agent, or Firm* — Morgan, Lewis & Bockius LLP

(57) ABSTRACT

An article of manufacture includes an array of distinct and separate regions with respective pharmaceutical compounds located thereon. The array of distinct and separate regions includes a first region with a first set of one or more pharmaceutical compounds located thereon; a second region, that is distinct and separate from the first region, with a second set of one or more pharmaceutical compounds, that is distinct from the first set of one or more pharmaceutical compounds, located thereon; and a third region, that is distinct and separate from the first region and the second region, with a third set of one or more pharmaceutical compounds, that is distinct from the first set of one or more pharmaceutical compounds and the second set of one or more pharmaceutical compounds, located thereon.

30 Claims, 16 Drawing Sheets

Related U.S. Application Data

(60) Provisional application No. 62/552,277, filed on Aug. 30, 2017.

(51) Int. Cl.
  *G01N 33/50* (2006.01)
  *G01N 33/00* (2006.01)

(52) U.S. Cl.
  CPC .... *G01N 33/5011* (2013.01); *B01L 2300/069* (2013.01); *B01L 2300/0829* (2013.01); *B01L 2300/0832* (2013.01); *G01N 33/0081* (2024.05); *G01N 2500/10* (2013.01)

(58) Field of Classification Search
  CPC ....... B01L 2300/0829; B01L 2300/089; G01N 35/00009
  See application file for complete search history.

(56) References Cited

U.S. PATENT DOCUMENTS

| | | | |
|---|---|---|---|
| 6,372,504 B1* | 4/2002 | Tervamaki | B01L 3/563 422/534 |
| 6,790,817 B2 | 9/2004 | Gladfelter et al. | |
| 2003/0119694 A1 | 6/2003 | Gladfelter et al. | |
| 2003/0148401 A1 | 8/2003 | Agrawal et al. | |
| 2004/0219074 A1* | 11/2004 | Childers | B01L 3/5085 422/534 |
| 2012/0000330 A1 | 1/2012 | Griffin | |
| 2018/0353956 A1* | 12/2018 | Bandara | B01L 3/502707 |

FOREIGN PATENT DOCUMENTS

| | | |
|---|---|---|
| JP | 2006507815 A | 3/2006 |
| JP | 2011527571 A | 11/2011 |
| JP | 2013536692 A | 9/2013 |
| JP | 2016533498 A | 10/2016 |

OTHER PUBLICATIONS

Imprimed Inc., International Search Report/Written Opinion, PCT/US2018/044306, Oct. 10, 2018, 8 pages.

ImpriMed, Inc., JP2020512836, Decision to Grant a Patent, Jul. 9, 2021, 5 pgs.

ImpriMed, Inc., JP2020512836, Notice of Reasons for Refusal, Mar. 4, 2021, 12 pgs.

ImpriMed, Inc., KR20207004848, Written Decision on Registration, Dec. 24, 2021, 4 pgs.

* cited by examiner

DEVICES AND METHODS FOR HIGH-THROUGHPUT SCREENING OF CHEMICAL AND BIOCHEMICAL COMPOUNDS

RELATED APPLICATIONS

This application is a continuation application of International Application No. PCT/US2018/044306, filed Jul. 30, 2018, which claims the benefit of, and priority to, U.S. Provisional Patent Application Ser. No. 62/552,277, filed Aug. 30, 2017. Both of these applications are incorporated by reference herein in their entireties.

FIELDS

This application relates to devices and methods for screening of chemical and/or biochemical compounds (e.g., pharmaceutical compounds).

BACKGROUND

In oncology, the efficacy of drug(s) is currently assessed based on imaging tumor cells in a patient's body before and after treatment with particular drug(s), and comparison of the "before treatment" image and the "after treatment" image to determine the reduction in the number and/or size of tumor cells or tumor cell clusters. While this approach has certain advantages, this process requires a "wait and watch" period, which often takes several weeks to months before an oncologist can evaluate whether or not prescribed drugs (and their assigned concentrations) are effective for a patient. If a patient is treated with non-effective drug(s), the disease progresses even further during this drug efficacy evaluation period, which is a critical problem in diseases like cancer or life-threatening infectious diseases.

Accordingly, there is a need for devices and methods that allow a rapid and cost-effective determination of drug efficacy.

SUMMARY

A number of embodiments that overcome the limitations and disadvantages of conventional devices and methods are presented in more detail below. These embodiments provide devices and methods for screening chemical and/or biochemical compounds (e.g., pharmaceutical compounds).

In accordance with some embodiments, an article of manufacture includes an array of distinct and separate regions with respective chemical and/or biochemical compounds (e.g., pharmaceutical compounds) located thereon. The array of distinct and separate regions includes a first region with a first set of one or more chemical and/or biochemical compounds located thereon; a second region, that is distinct and separate from the first region, with a second set of one or more chemical and/or biochemical compounds, that is distinct from the first set of one or more chemical and/or biochemical compounds, located thereon; and a third region, that is distinct and separate from the first region and the second region, with a third set of one or more chemical and/or biochemical compounds, that is distinct from the first set of one or more chemical and/or biochemical compounds and the second set of one or more chemical and/or biochemical compounds, located thereon.

In some embodiments, the array of distinct and separate regions includes a fourth region, that is distinct and separate from the first region, the second region, and the third region, with a fourth set of one or more chemical and/or biochemical compounds, that is distinct from the first set of one or more chemical and/or biochemical compounds, the second set of one or more chemical and/or biochemical compounds, and the third set of one or more chemical and/or biochemical compounds, located thereon.

In some embodiments, the article of manufacture further includes one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located.

In some embodiments, the first region and the second region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The first region and the third region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The first region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The second region and the third region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The second region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The third region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located.

In some embodiments, the article of manufacture further includes a well plate (e.g., a micro-well plate) defining an array of distinct wells. A respective well of the array of distinct wells includes a respective region of the array of distinct and separate regions.

In some embodiments, the article of manufacture includes an insert having an array of dippers that are positioned to correspond to an array of distinct wells of a well plate, a respective dipper of the array of dippers including a respective region of the array of distinct and separate regions.

In some embodiments, the respective dipper includes a permeable membrane with a respective set of one or more chemical and/or biochemical compounds located thereon.

In some embodiments, the article of manufacture further includes a sheet with the array of distinct and separate regions with respective compounds located thereon.

In some embodiments, the article of manufacture is the sheet with the array of distinct and separate regions with respective compounds located thereon.

In some embodiments, the sheet is at least partially water-soluble.

In some embodiments, the sheet defines, for a respective region of the array of distinct and separate regions, one or more through holes so that the respective region is connected to a rest of the sheet by one or more connecting regions.

In some embodiments, each of the one or more connecting regions has a shape of a spoke connecting the respective region to the rest of the sheet, the one or more connecting regions arranged around the respective region.

In some embodiments, the first set of one or more chemical and/or biochemical compounds, the second set of one or more chemical and/or biochemical compounds, and the third set of one or more chemical and/or biochemical compounds include one or more chemical and/or biochemical compounds selected from a group consisting of (i) one or more cancer drugs and (ii) one or more antibiotics.

In some embodiments, the first set of one or more chemical and/or biochemical compounds, the second set of one or more chemical and/or biochemical compounds, and the third set of one or more chemical and/or biochemical compounds include either one or more cancer drugs or one or more antibiotics.

In some embodiments, the first set of one or more chemical and/or biochemical compounds includes one or more water-soluble compounds. The second set of one or more chemical and/or biochemical compounds includes one or more water-soluble compounds. The third set of one or more chemical and/or biochemical compounds includes one or more water-soluble compounds.

In some embodiments, the first set of one or more chemical and/or biochemical compounds includes one or more chemical and/or biochemical compounds that are soluble to a solvent that is not water. The second set of one or more chemical and/or biochemical compounds includes one or more chemical and/or biochemical compounds that are soluble to the solvent that is not water. The third set of one or more chemical and/or biochemical compounds includes one or more chemical and/or biochemical compounds that are soluble to a solvent that is not water.

In some embodiments, the first set of one or more chemical and/or biochemical compounds includes a first compound at a first concentration. The second set of one or more chemical and/or biochemical compounds includes the first compound at a second concentration that is distinct from the first concentration. The third set of one or more chemical and/or biochemical compounds includes the first compound at a third concentration that is distinct from the first concentration and the second concentration.

In some embodiments, the first compound is a cancer drug or an antibiotic.

In some embodiments, the first set of one or more chemical and/or biochemical compounds includes a second compound at a fourth concentration. The second set of one or more chemical and/or biochemical compounds includes the second compound at a fifth concentration that is distinct from the fourth concentration. The third set of one or more chemical and/or biochemical compounds includes the second compound at a sixth concentration that is distinct from the fourth concentration and the fifth concentration.

In some embodiments, the second compound is a cancer drug or an antibiotic; and the second compound is distinct from the first compound. In some embodiments, the first compound is a first cancer drug and the second compound is a second cancer drug that is distinct from the first cancer drug. In some embodiments, the first compound is a first antibiotic and the second compound is a second antibiotic that is distinct from the first antibiotic.

In some embodiments, the first set of one or more chemical and/or biochemical compounds includes a first amount of a first compound. The second set of one or more chemical and/or biochemical compounds includes a second amount of the first compound. The second amount is distinct from the first amount. The third set of one or more chemical and/or biochemical compounds includes a third amount of the first compound. The third amount is distinct from the first amount and the second amount.

In some embodiments, the first set of one or more chemical and/or biochemical compounds includes a fourth amount of a second compound. The second set of one or more chemical and/or biochemical compounds includes a fifth amount of the second compound. The fifth amount is distinct from the fourth amount. The third set of one or more chemical and/or biochemical compounds includes a sixth amount of the second compound. The sixth amount is distinct from the fourth amount and the fifth amount.

In some embodiments, the first set of one or more chemical and/or biochemical compounds includes a particular release control reagent. The second set of one or more chemical and/or biochemical compounds includes the particular release control reagent. The third set of one or more chemical and/or biochemical compounds includes the particular release control reagent.

In some embodiments, the first set of one or more chemical and/or biochemical compounds includes a seventh amount of the particular release control reagent. The second set of one or more chemical and/or biochemical compounds includes the seventh amount of the particular release control reagent. The third set of one or more chemical and/or biochemical compounds includes the seventh amount of the particular release control reagent.

In some embodiments, the first set of one or more chemical and/or biochemical compounds includes a seventh amount of the particular release control reagent. The second set of one or more chemical and/or biochemical compounds includes an eighth amount of the particular release control reagent, the eighth amount being distinct from the seventh amount. The third set of one or more chemical and/or biochemical compounds includes a ninth amount of the particular release control reagent, the ninth amount being distinct from the seventh amount and the eighth amount.

In some embodiments, the first set of one or more chemical and/or biochemical compounds includes a particular growth control reagent. The second set of one or more chemical and/or biochemical compounds includes the particular growth control reagent. The third set of one or more chemical and/or biochemical compounds includes the particular growth control reagent.

In some embodiments, the first set of one or more chemical and/or biochemical compounds includes a tenth amount of the particular growth control reagent. The second set of one or more chemical and/or biochemical compounds includes the tenth amount of the particular growth control reagent. The third set of one or more chemical and/or biochemical compounds includes the tenth amount of the particular growth control reagent.

In some embodiments, the first set of one or more chemical and/or biochemical compounds includes a tenth amount of the particular growth control reagent. The second set of one or more chemical and/or biochemical compounds includes an eleventh amount of the particular growth control reagent. The eleventh amount is distinct from the tenth amount. The third set of one or more chemical and/or biochemical compounds includes a twelfth amount of the particular growth control reagent. The twelfth amount is distinct from the tenth amount and the eleventh amount.

In accordance with some embodiments, a method includes obtaining any sheet described herein. The method also includes obtaining a well plate defining an array of distinct wells, the array of distinct wells including a first well, a second well that is distinct from the first well, and a third well that is distinct from the first well and the second well; removing, from the sheet, the first region of the sheet and dispensing the first region of the sheet into the first well; removing, from the sheet, the second region of the sheet and dispensing the second region of the sheet into the second well; and removing, from the sheet, the third region of the sheet and dispensing the third region of the sheet into the third well.

In some embodiments, the first region of the sheet, the second region of the sheet, and the third region of the sheet are concurrently removed and dispensed into respective wells.

In accordance with some embodiments, a method includes obtaining any well plate described herein.

In some embodiments, the method further includes providing a first portion of a sample in the first well; providing a second portion of the sample in the second well; and providing a third portion of the sample in the third well.

In some embodiments, the method further includes incubating the first portion of the sample in the first well; incubating the second portion of the sample in the second well; and incubating the third portion of the sample in the third well.

In some embodiments, the method further includes determining an amount of the sample in the first well; determining an amount of the sample in the second well; and determining an amount of the sample in the third well.

In some embodiments, the method further includes selecting a particular set of one or more chemical and/or biochemical compounds based on the amount of the sample in the first well, the amount of the sample in the second well, and the amount of the sample in the third well.

In some embodiments, the method further includes treating a patient with one or more chemical and/or biochemical compounds based on selection of the particular set of one or more chemical and/or biochemical compounds.

In some embodiments, the method further includes selecting a composition of one or more chemical and/or biochemical compounds for treating a patient based on selection of the particular set of one or more chemical and/or biochemical compounds.

In accordance with some embodiments, a punching device for dispensing a plurality of respective regions of a sheet into respective wells of a well plate. The device includes a frame defining a reference plane; and a plurality of pillars mounted on the frame. A respective pillar of the plurality of pillars is mounted substantially perpendicular to the reference plane.

In some embodiments, each pillar of the plurality of pillars is a cylindrical pillar.

In some embodiments, each pillar of the plurality of pillars is hollow at least in a portion that is located away from the frame.

In some embodiments, devices and methods described herein replace traditional devices and methods for screening chemical and/or biochemical compounds. In some embodiments, devices and methods described herein complement traditional devices and methods for screening chemical and/or biochemical compounds.

BRIEF DESCRIPTION OF THE DRAWINGS

The embodiments will be better understood with reference to the detailed description when considered in conjunction with the non-limiting examples and the accompanying drawings.

Like reference numerals refer to corresponding parts throughout the figures.

DETAILED DESCRIPTION

Figure 1:
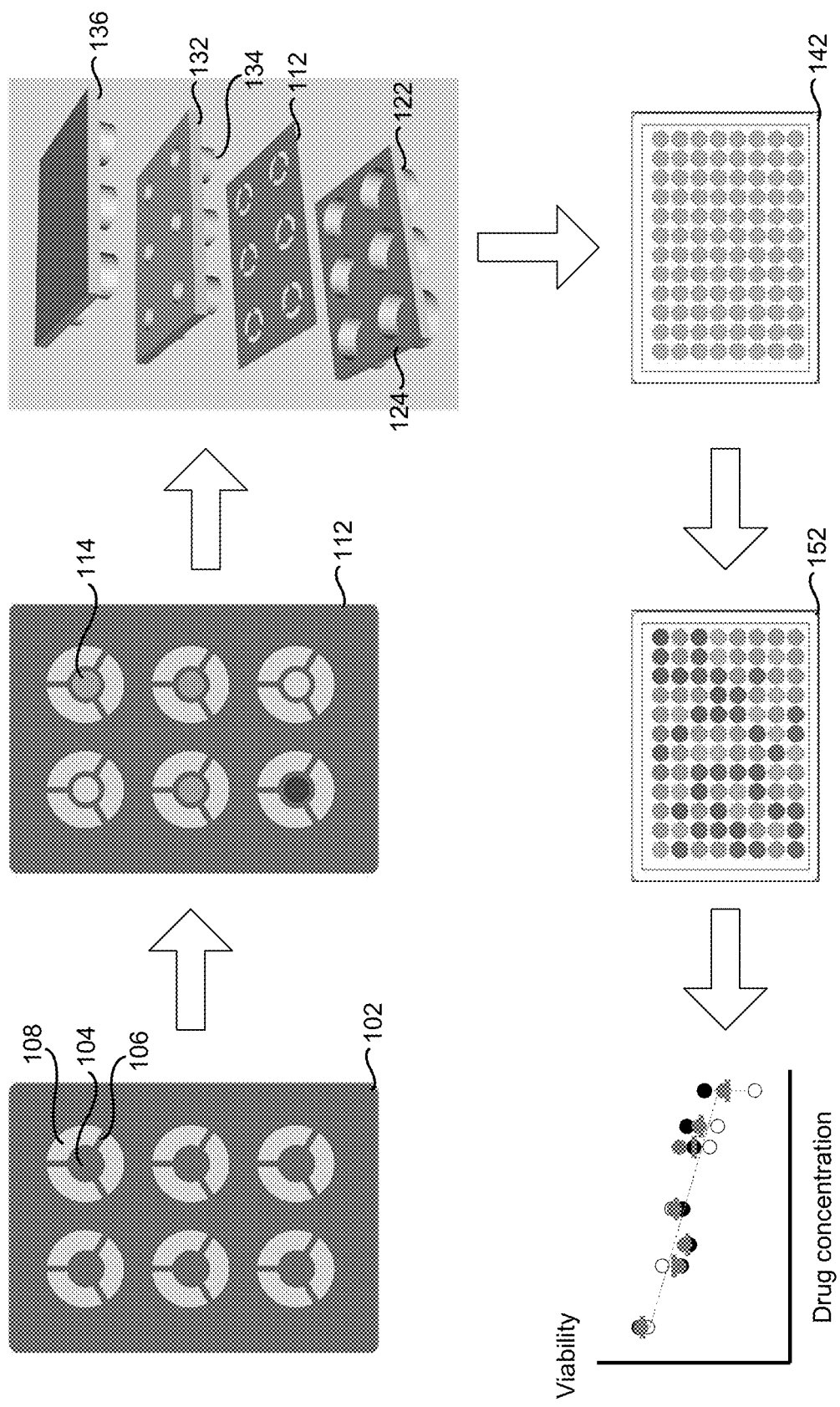
FIG. 1 depicts an example workflow in accordance with some embodiments.

As described above, conventional screening has many limitations. Ex vivo phenotypic screening is a promising approach to overcome these limitations. Under this approach, for example in cancer, the efficacy of drug(s) is evaluated by sampling tumor cells from patients and analyzing cellular responses ex vivo. The time required for efficacy assessment is significantly shorter (in the order of days or one to two weeks); therefore, a cancer patient can be treated with the most effective drug combination specific to a given phenotype of the patient's cancer sooner than with the conventional screening method.

Despite this significant potential, phenotypic screening technologies are not widely adopted. The difficulties are mainly associated with the limited number of drug combinations that can be tested and the limited lifetime of primary tumor cells in an ex vivo environment. These limitations and disadvantages are overcome by devices and methods presented herein.

The devices and methods described herein use an array of regions predisposed to chemical and/or biochemical compounds to facilitate the high-throughput phenotypic screening. Utilizing the array of regions predisposed to chemical and/or biochemical compounds eliminates the need for pipetting the chemical and/or biochemical compounds into separate wells, thereby reducing errors associated with multiple pipetting operations and improving the accuracy in screening assays. In addition, utilizing the array of regions predisposed to chemical and/or biochemical compounds allows concurrent preparation of multiple wells and reduces the time required to prepare a well plate for phenotypic screening, thereby improving the throughput of the phenotypic screening.

Reference will now be made in detail to embodiments, examples of which are illustrated in the accompanying drawings. In the following detailed description, numerous specific details are set forth in order to provide a thorough understanding of the various embodiments described herein. However, it will be apparent to one of ordinary skill in the art that the various embodiments described herein may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first region could be termed a second region, and, similarly, a second region could be termed a first region, without departing from the scope of the various described embodiments. The first region and the second region are both regions, but they are not the same region, unless the context clearly indicates otherwise.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

FIG. 1 depicts an example workflow in accordance with some embodiments.

In FIG. 1, sheet 102 (e.g., a paper or a transparent film) is obtained. In FIG. 1, multiple holes 108 are defined in sheet 102 so that region 104 of sheet 102 is connected to the rest of sheet 102 via multiple bridges 106. In some embodiments, region 104 is called a central region (without limiting the embodiments to having region 104 in a center of bridges 106).

Although sheet 102 has a 2-by-3 array of regions, in some embodiments, sheet 102 has a larger number of regions (e.g., a 12-by-8 array or a 24-by-16 array).

FIG. 1 also shows that one or more chemical and/or biochemical compounds are disposed on central regions 114 to form sheet 112. In FIG. 1, a unique combination of chemical and/or biochemical compounds is disposed on each central region.

FIG. 1 further shows that sheet 112 is placed over well-plate 122 with a plurality of wells 124, and one or more loading devices 132 and/or 136 are used to release portions of sheet 112 (e.g., central regions) from the rest of sheet 112. The released portions of sheet 112 are placed in wells of well-plate 122. Loading device 132 and/or loading device 136 include release components 134 (e.g., blades) configured to release the portions of sheet 112 from the rest of sheet 112.

In addition, FIG. 1 shows that the released portions of sheet 112 in the wells of well-plate 122 are used to treat cells located in the wells of well-plate 122.

In some embodiments, the cells are incubated in the wells of well-plate 122 (e.g., for 1-3 days) in presence of the one or more chemical and/or biochemical compounds at least initially disposed on respective released portions of sheet 112.

After the incubation, any cellular response (e.g., changes in the amount of cells, cell death, cell apoptosis, dynamic change in a cellular marker) in each well of incubated well-plate 152 is determined (e.g., using colorimetric measurements or fluorescence measurements).

From the measurements, the effect of particular combinations of one or more chemical and/or biochemical compounds is determined (e.g., a cell viability is plotted as a function of drug concentrations).

Figure 2A:
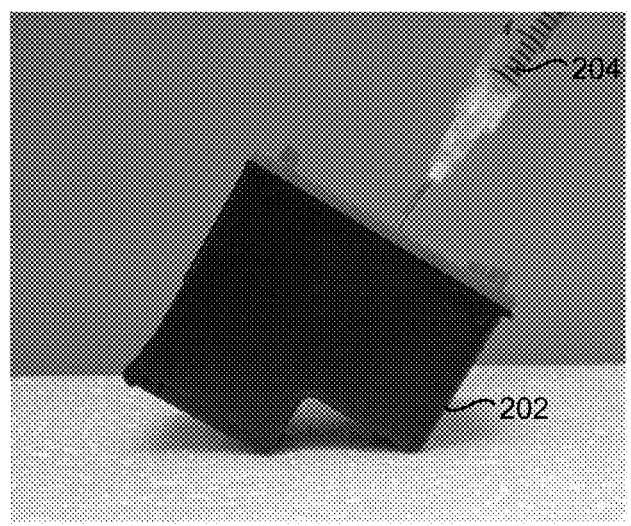
FIG. 2A illustrates loading a pharmaceutical compound in an inkjet cartridge in accordance with some embodiments.

FIG. 2A illustrates loading a pharmaceutical compound in a cartridge in accordance with some embodiments.

In some embodiments, the cartridge is an inkjet cartridge. In some embodiments, the inkjet cartridge includes dye molecules. In some other embodiments, the inkjet cartridge does not include dye molecules. In some embodiments, a pharmaceutical compound (e.g., doxorubicin, which is a widely used chemotherapy agent) is injected into the inkjet cartridge. In some embodiments, cartridge is used for subsequent creation of the array of regions using an inkjet printer.

Figure 2B:
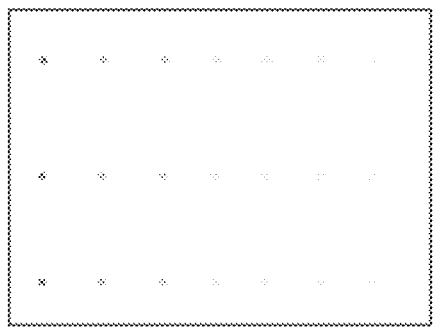
FIG. 2B illustrates an array of doxorubicin printed on a sheet in accordance with some embodiments.

FIG. 2B illustrates an array of doxorubicin printed on a sheet in accordance with some embodiments. The inkjet cartridge containing doxorubicin was used with an inkjet printer to print on a sheet the pattern shown in FIG. 2B. In some embodiments, the sheet was sterilized prior to printing the patterns thereon. By utilizing the CMYK color adjustment setting, the amount of doxorubicin printed on each spot was adjusted. The color intensity of each spot indicates the amount and/or concentration of doxorubicin (and/or dye molecules) on the spot.

In some embodiments, the array of chemical and/or biochemical compounds is dried for transportation of the sheet (e.g., the sheet is sold with the array of dried chemical and/or biochemical compounds thereon). In some embodiments, the array of chemical and/or biochemical compounds is coated or covered with another material (e.g., a protective soluble film is disposed over the array of chemical and/or biochemical compounds).

Figure 2C:
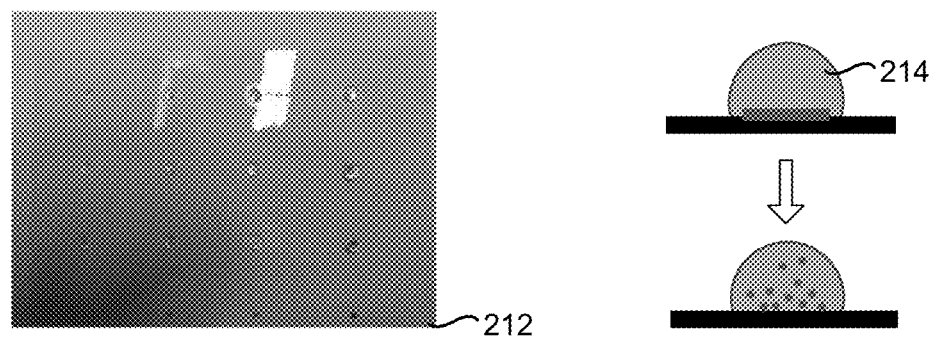
FIG. 2C illustrates the array of doxorubicin that is printed and re-dissolved in a solvent in accordance with some embodiments.

FIG. 2C illustrates the array of doxorubicin that is printed and re-dissolved in a solvent in accordance with some embodiments. The left side image of FIG. 2C illustrates an array of doxorubicin on the sheet with a droplet of a solvent (e.g., water) added to each spot. The right side drawing of FIG. 2C illustrates that the addition of water droplet 214 causes the one or more chemical and/or biochemical compounds to dissolve in water droplet 214. In some embodiments, the one or more chemical and/or biochemical compounds are used to treat cells (e.g., cells are exposed to the one or more chemical and/or biochemical compounds dissolved in the solvent). In some embodiments, the viability of the cells (e.g., the amount and/or size of the cells) is determined after treating the cells with the one or more chemical and/or biochemical compounds.

Figure 2D:
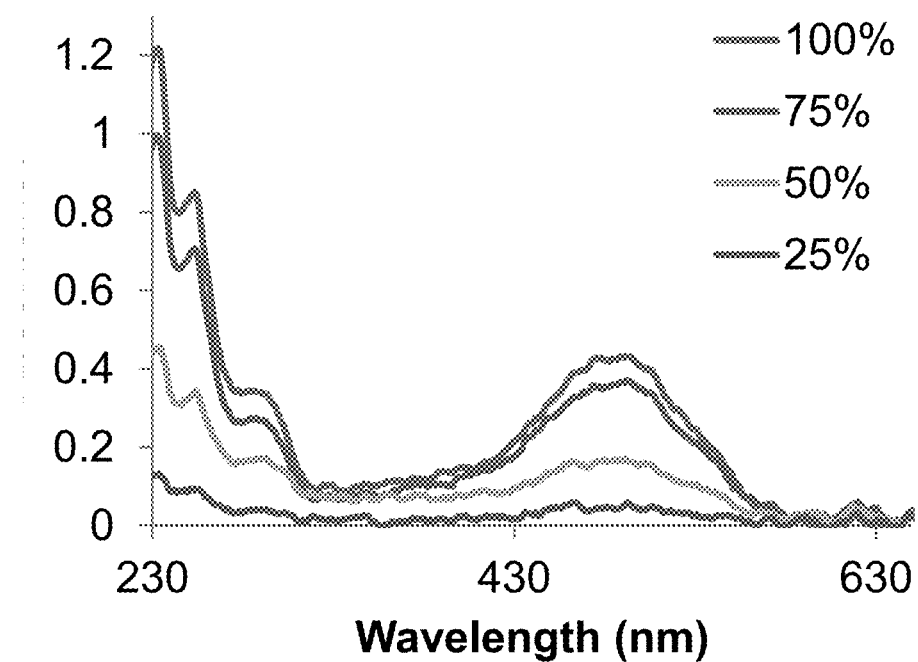
FIG. 2D illustrates absorbance spectra of the array of doxorubicin that is re-dissolved in a solvent in accordance with some embodiments.

FIG. 2D illustrates absorbance spectra of the array of doxorubicin that is re-dissolved in a solvent in accordance with some embodiments. The absorbance spectra shown in FIG. 2D were obtained by using a spectrophotometer. The absorbance spectra show that a spot with a high concentration of doxorubicin has a high absorbance peak (e.g., around 480 nm) and a spot with a low concentration of doxorubicin has a low absorbance peak.

Figure 2E:
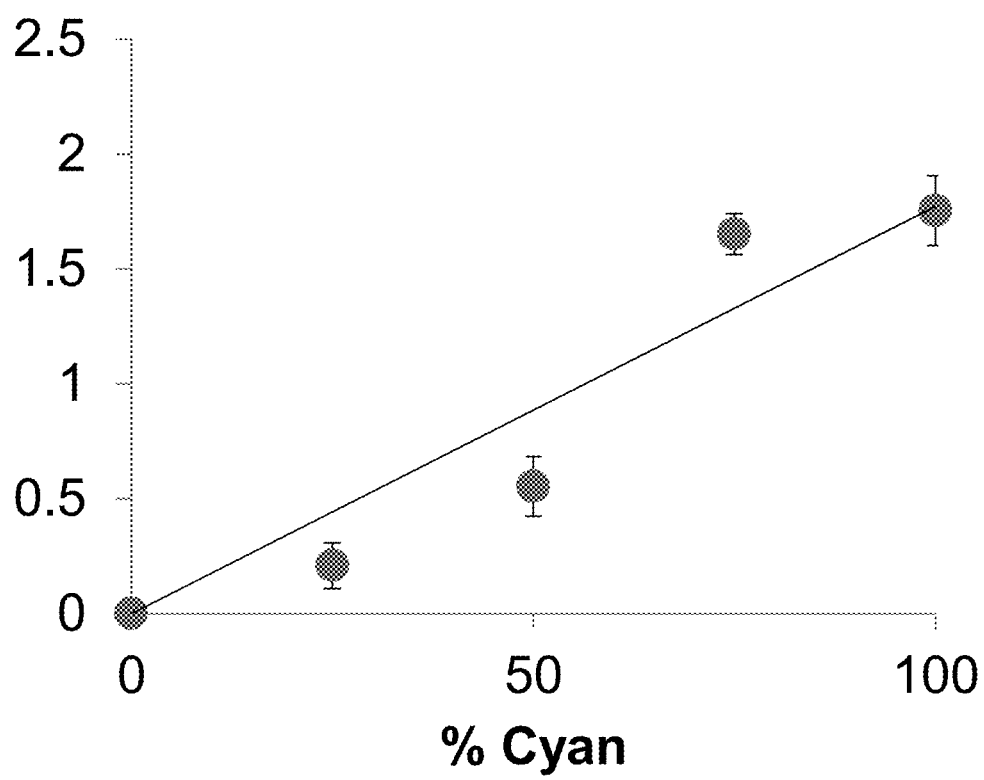
FIG. 2E shows amounts of doxorubicin for various printing conditions in accordance with some embodiments.

FIG. 2E shows concentrations of doxorubicin for various printing conditions in accordance with some embodiments. The chart depicted in FIG. 2E shows that there is a substantially linear correlation between a color intensity setting and a concentration of doxorubicin (e.g., the $R^2$ value of 0.90).

In some embodiments, amounts of cells are determined based on concentrations of chemical and/or biological compounds. In some embodiments, concentrations of chemical and/or biological compounds that correspond to a low amount of cells are selected (e.g., for treating tumor cells). For example, concentrations of chemical and/or biological compounds that result in a low amount of cells are selected. In some embodiments, concentrations of chemical and/or biological compounds that correspond to a high amount of cells are selected (e.g., for treating infected cells). For example, concentrations of chemical and/or biological compounds that result in a high amount of cells are selected.

Although FIGS. 2A-2E illustrate examples with doxorubicin, a person having ordinary skill in the art would understand that other chemical and/or biochemical compounds can be used (e.g., other types of cancer drugs and/or other pharmaceuticals, such as antibiotics).

Figure 3A:
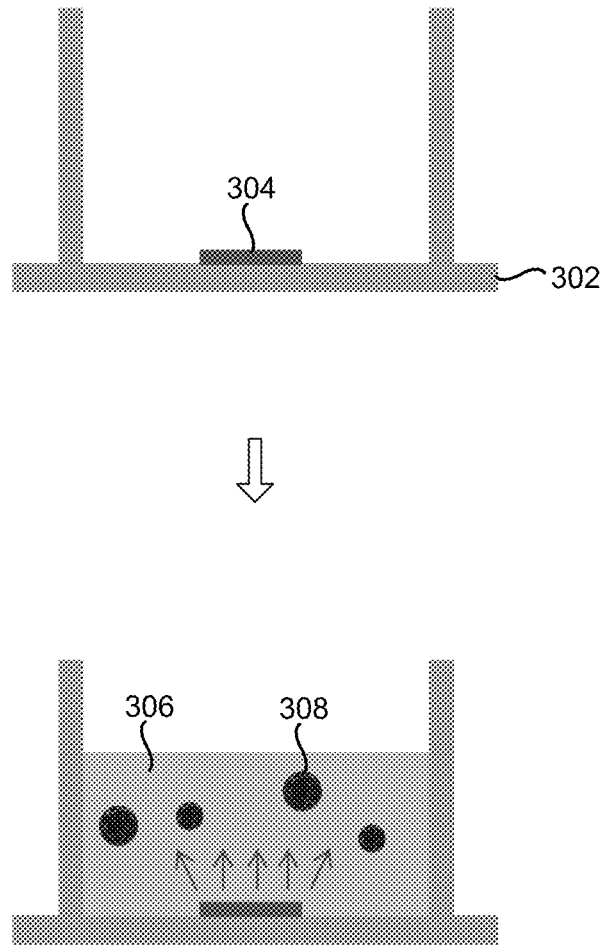
FIG. 3A illustrates a well plate with one or more chemical and/or biochemical compounds directly disposed thereon in accordance with some embodiments.

FIG. 3A illustrates well plate 302 (e.g., a micro-well plate) with chemical and/or biochemical compounds 304 directly disposed thereon (e.g., in a well of well plate 302) in accordance with some embodiments. In some embodiments, chemical and/or biochemical compounds 304 are directly disposed on well plate 302 by printing chemical and/or biochemical compounds 304 on well plate 302.

FIG. 3A also illustrates that cell culture media 306 and cancer cells 308 are placed in the well of well plate 302, thereby releasing chemical and/or biochemical compounds 304 (e.g., a cancer drug) into cell culture media 306. The released chemical and/or biochemical compounds 304 interact with cancer cells 308, and the effect of chemical and/or biochemical compounds 304 (e.g., the viability of cancer cells 308 in response to an exposure to chemical and/or biochemical compounds 304) is subsequently determined (e.g., the amount and/or size of cancer cells 308 are measured after an incubation).

Figure 3B:
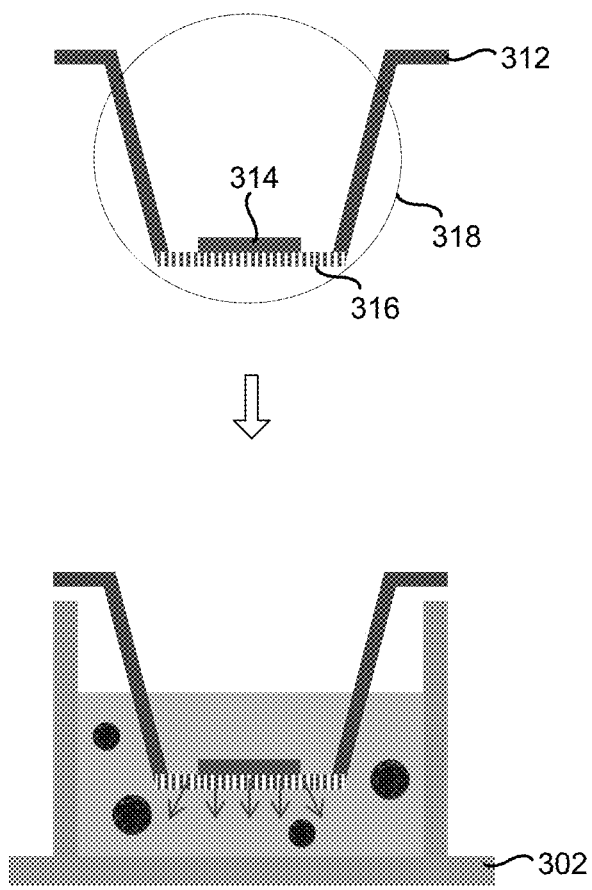
FIG. 3B illustrates an insert for a well plate in accordance with some embodiments.

FIG. 3B illustrates insert 312 for a well plate in accordance with some embodiments. In some embodiments, insert 312 includes a top surface and one or more dippers 318 that extend below the top surface (e.g., for immersion into a solvent and/or cell culture media in the well plate). In some embodiments, insert 312 includes a plurality of dippers 318 positioned at located that correspond to wells of the well plate (e.g., insert 312 has 96 dippers positioned for insertion into the wells of a 96 well plate so that a first dipper is configured for insertion into a first well of the well plate, a second dipper is configured for insertion into a second well of the well plate, and so on). In FIG. 3B, insert 312 includes permeable membrane 316 and chemical and/or biochemical compounds 314 disposed thereon.

When insert 312 is placed at least partially into a well of well plate 302, chemical and/or biochemical compounds 314 disposed on insert 312 are released into cell culture media in the well of well plate 302. Released chemical and/or biochemical compounds 314 interact with cancer cells in the solvent.

Figure 3C:
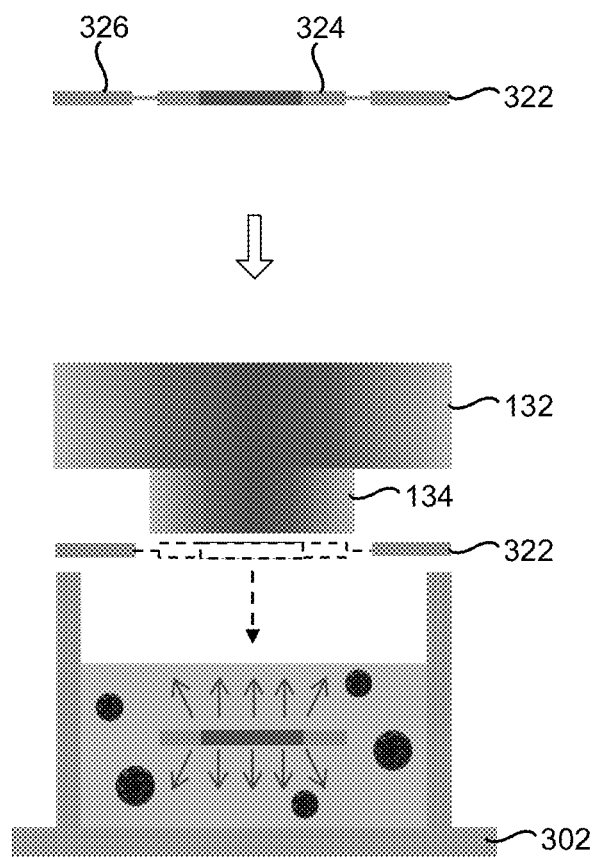
FIG. 3C illustrates a sheet with one or more chemical and/or biochemical compounds disposed thereon and the use of the sheet with a loading device in accordance with some embodiments.

FIG. 3C illustrates sheet 322 with one or more chemical and/or biochemical compounds disposed thereon in accordance with some embodiments. Sheet 322 includes first region 324 with the one or more chemical and/or biochemical compounds disposed thereon and second region 326.

In use, sheet 322 is placed over well plate 302 and loading device 132 is used to release first region 324 of sheet 322 from second region 326 of sheet 322. In some embodiments, sheet 322 is aligned with well plate 302 so that first region 324 of sheet 322 is placed over a particular well of well plate 302. Release first region 324 is dropped into a well of well plate 302. The one or more chemical and/or biochemical compounds disposed on first region 324 of sheet 322 are released into cell culture media in the well of well plate 302. The released chemical and/or biochemical compounds interact with cancer cells in the cell culture media. In some embodiments, the cell culture media and/or the cancer cells are placed in the well of well plate 302 before releasing first region 324 of sheet 322 from second region 326 of sheet 322 into the well of well plate 302. In some embodiments, the cell culture media and/or the cancer cells are placed in the well of well plate 302 after releasing first region 324 of sheet 322 from second region 326 of sheet 322 into the well of well plate 302. In some embodiments, one of the cell culture media and the cancer cells is placed in the well of well plate 302 before releasing first region 324 of sheet 322 from second region 326 of sheet 322 into the well of well plate 302, and the other of the cell culture media and the cancer cells is placed in the well of well plate 302 after releasing first region 324 of sheet 322 from second region 326 of sheet 322 into the well of well plate 302 (e.g., the cell culture media are placed in the well of well plate 302 before releasing first region 324 of sheet 322 from second region 326 of sheet 322 into the well of well plate 302 and the cancer cells are placed in the well of well plate 302 after releasing first region 324 of sheet 322 from second region 326 of sheet 322 into the well of well plate 302).

Although FIGS. 3A-3C illustrate examples with cancer cells in well plate 302, a person having ordinary skill in the art would understand that analogous operations can be performed with other cells (e.g., infecting cells and/or infected cells). In such embodiments, the one or more chemical and/or biochemical compounds include one or more anti-infection compounds (e.g., antibiotics).

Figure 4A:
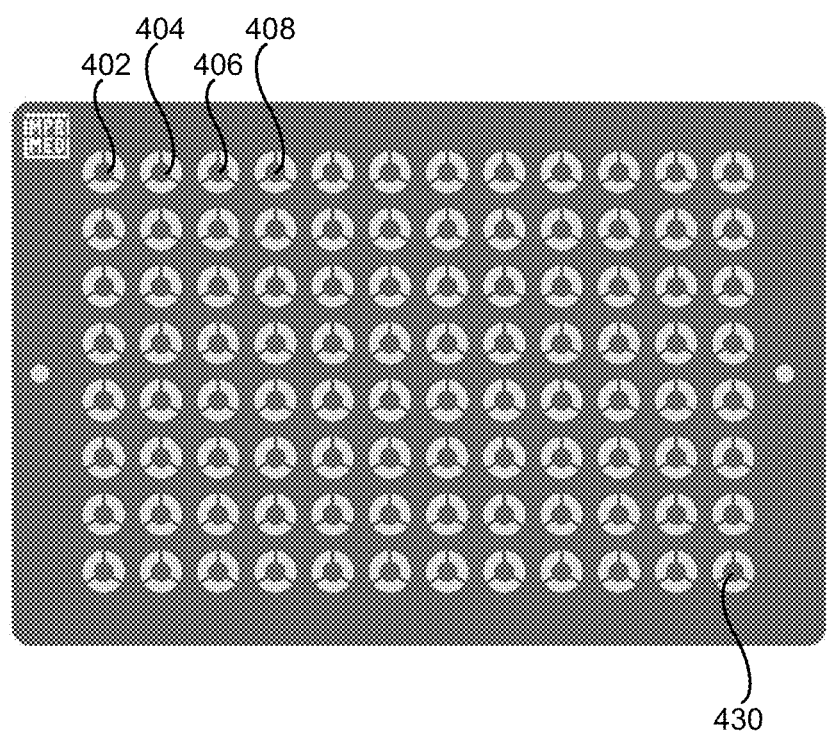
FIG. 4A illustrates a sheet with one or more chemical and/or biochemical compounds disposed thereon in accordance with some embodiments.

FIG. 4A illustrates a sheet with one or more chemical and/or biochemical compounds disposed thereon in accordance with some embodiments. The sheet shown in FIG. 4A includes an array of regions, and a respective set of one or more chemical and/or biochemical compounds is disposed on a respective region. For example, FIG. 4A shows region 402, region 404, region 406, and region 408 of the array of regions.

In some embodiments, at least a subset of regions 402, region 404, region 406, and region 408 includes a first chemical and/or biochemical compound. In some embodiments, regions 402, region 404, region 406, and region 408 all include the first chemical and/or biochemical compound. In some embodiments, regions 402, region 404, region 406, and region 408 all include the first chemical and/or biochemical compound at a first concentration. In some embodiments, regions 402, region 404, region 406, and region 408 include the first chemical and/or biochemical compound at different concentrations (e.g., region 402 includes the first chemical at a first concentration, region 404 includes the first chemical at a second concentration that is distinct from the first concentration, region 406 includes the first chemical at a third concentration that is distinct from the first concentration and the second concentration, and region 408 includes the first chemical at a fourth concentration that is distinct from the first concentration, the second concentration, and the third concentration).

In some embodiments, at least a subset of regions 402, region 404, region 406, and region 408 includes a second chemical and/or biochemical compound. In some embodiments, regions 402, region 404, region 406, and region 408 all include the second chemical and/or biochemical compound. In some embodiments, regions 402, region 404, region 406, and region 408 all include the second chemical and/or biochemical compound at a fifth concentration. In some embodiments, regions 402, region 404, region 406, and region 408 include the second chemical and/or biochemical compound at different concentrations (e.g., region 402 includes the second chemical at a fifth concentration, region 404 includes the second chemical at a sixth concentration that is distinct from the fifth concentration, region 406 includes the second chemical at a seventh concentration that is distinct from the fifth concentration and the sixth concentration, and region 408 includes the second chemical at an eighth concentration that is distinct from the fifth concentration, the sixth concentration, and the seventh concentration).

In some embodiments, at least a subset of regions 402, region 404, region 406, and region 408 includes a third chemical and/or biochemical compound. In some embodiments, regions 402, region 404, region 406, and region 408 all include the third chemical and/or biochemical compound. In some embodiments, regions 402, region 404, region 406, and region 408 all include the third chemical and/or biochemical compound at a ninth concentration. In some embodiments, regions 402, region 404, region 406, and region 408 include the third chemical and/or biochemical compound at different concentrations (e.g., region 402 includes the third chemical at a ninth concentration, region 404 includes the third chemical at a tenth concentration that is distinct from the ninth concentration, region 406 includes the third chemical at a eleventh concentration that is distinct from the ninth concentration and the tenth concentration, and region 408 includes the third chemical at a twelfth concentration that is distinct from the ninth concentration, the tenth concentration, and the eleventh concentration).

In some embodiments, at least a subset of regions 402, region 404, region 406, and region 408 includes a fourth chemical and/or biochemical compound. In some embodiments, regions 402, region 404, region 406, and region 408 all include the fourth chemical and/or biochemical compound. In some embodiments, regions 402, region 404, region 406, and region 408 all include the fourth chemical and/or biochemical compound at a thirteenth concentration. In some embodiments, regions 402, region 404, region 406, and region 408 include the fourth chemical and/or biochemical compound at different concentrations (e.g., region 402 includes the fourth chemical at a thirteenth concentration, region 404 includes the fourth chemical at a fourteenth concentration that is distinct from the thirteenth concentration, region 406 includes the fourth chemical at a fifteenth concentration that is distinct from the thirteenth concentration and the fourteenth concentration, and region 408 includes the fourth chemical at a sixteenth concentration that is distinct from the thirteenth concentration, the fourteenth concentration, and the fifteenth concentration).

In some embodiments, at least a subset of regions 402, region 404, region 406, and region 408 includes a first chemical and/or biochemical compound. In some embodiments, regions 402, region 404, region 406, and region 408 all include the first chemical and/or biochemical compound. In some embodiments, regions 402, region 404, region 406, and region 408 all include the first chemical and/or biochemical compound at a first amount. In some embodiments, regions 402, region 404, region 406, and region 408 include the first chemical and/or biochemical compound at different amounts (e.g., region 402 includes the first chemical at a first amount, region 404 includes the first chemical at a second amount that is distinct from the first amount, region 406 includes the first chemical at a third amount that is distinct from the first amount and the second amount, and region 408 includes the first chemical at a fourth amount that is distinct from the first amount, the second amount, and the third amount).

In some embodiments, at least a subset of regions 402, region 404, region 406, and region 408 includes a second chemical and/or biochemical compound. In some embodiments, regions 402, region 404, region 406, and region 408 all include the second chemical and/or biochemical compound. In some embodiments, regions 402, region 404, region 406, and region 408 all include the second chemical and/or biochemical compound at a fifth amount. In some embodiments, regions 402, region 404, region 406, and region 408 include the second chemical and/or biochemical compound at different amounts (e.g., region 402 includes the second chemical at a fifth amount, region 404 includes the second chemical at a sixth amount that is distinct from the fifth amount, region 406 includes the second chemical at a seventh amount that is distinct from the fifth amount and the sixth amount, and region 408 includes the second chemical at an eighth amount that is distinct from the fifth amount, the sixth amount, and the seventh amount).

In some embodiments, at least a subset of regions 402, region 404, region 406, and region 408 includes a third chemical and/or biochemical compound. In some embodiments, regions 402, region 404, region 406, and region 408 all include the third chemical and/or biochemical compound. In some embodiments, regions 402, region 404, region 406, and region 408 all include the third chemical and/or biochemical compound at a ninth amount. In some embodiments, regions 402, region 404, region 406, and region 408 include the third chemical and/or biochemical compound at different amounts (e.g., region 402 includes the third chemical at a ninth amount, region 404 includes the third chemical at a tenth amount that is distinct from the ninth amount, region 406 includes the third chemical at a eleventh amount that is distinct from the ninth amount and the tenth amount, and region 408 includes the third chemical at a twelfth amount that is distinct from the ninth amount, the tenth amount, and the eleventh amount).

In some embodiments, at least a subset of regions 402, region 404, region 406, and region 408 includes a fourth chemical and/or biochemical compound. In some embodiments, regions 402, region 404, region 406, and region 408 all include the fourth chemical and/or biochemical compound. In some embodiments, regions 402, region 404, region 406, and region 408 all include the fourth chemical and/or biochemical compound at a thirteenth amount. In some embodiments, regions 402, region 404, region 406, and region 408 include the fourth chemical and/or biochemical compound at different amounts (e.g., region 402 includes the fourth chemical at a thirteenth amount, region 404 includes the fourth chemical at a fourteenth amount that is distinct from the thirteenth amount, region 406 includes the fourth chemical at a fifteenth amount that is distinct from the thirteenth amount and the fourteenth amount, and region 408 includes the fourth chemical at a sixteenth amount that is distinct from the thirteenth amount, the fourteenth amount, and the fifteenth amount).

In some embodiments, the sheet also includes region 430, as shown in FIG. 4A. No chemical or biochemical compound is disposed on region 430. In some embodiments, region 430 is used as a negative control in screening assays.

Figure 4B:
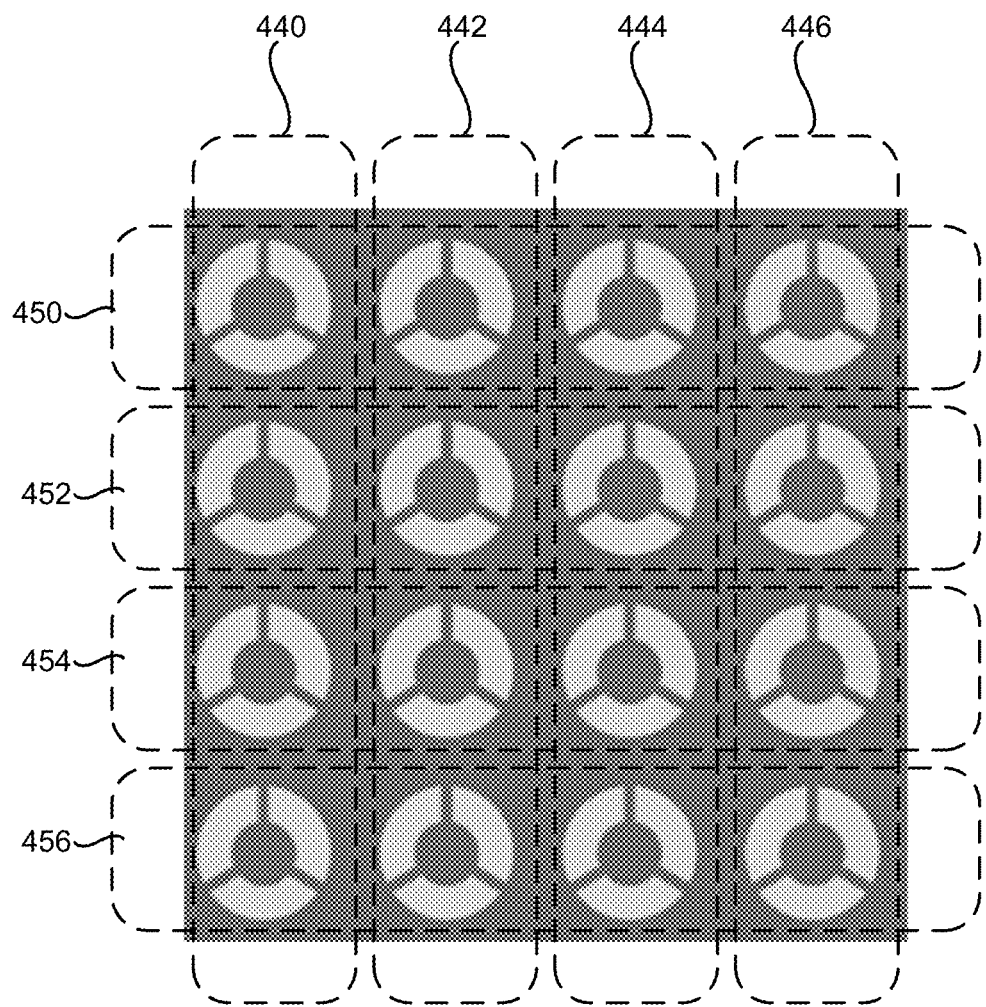
FIG. 4B illustrates an enlarged view of FIG. 4A in accordance with some embodiments.

FIG. 4B illustrates an enlarged view of FIG. 4A in accordance with some embodiments.

In some embodiments, regions located in column 440 include a first chemical or biochemical compound at a first concentration, regions located in column 442 include the first chemical or biochemical compound at a second concentration that is distinct from the first concentration, regions located in column 444 include the first chemical or biochemical compound at a third concentration that is distinct from the first concentration and the second concentration, and regions located in column 446 include the first chemical or biochemical compound at a fourth concentration that is distinct from the first concentration, the second concentration, and the third concentration. In addition, regions located in row 450 include a second chemical or biochemical compound at a fifth concentration, regions located in row 452 include the second chemical or biochemical compound at a sixth concentration that is distinct from the fifth concentration, regions located in row 454 include the second chemical or biochemical compound at a seventh concentration that is distinct from the fifth concentration and the sixth concentration, and regions located in row 456 include the second chemical or biochemical compound at an eighth concentration that is distinct from the fifth concentration, the sixth concentration, and the seventh concentration. For example, the region located within column 440 and row 450 has the first concentration of the first chemical and the fifth concentration of the second chemical disposed thereon, the region located within column 442 and row 454 has the second concentration of the first chemical and the seventh concentration of the second chemical disposed thereon, and the region located within column 446 and row 456 has the fourth concentration of the first chemical and the eighth concentration of the second chemical disposed thereon.

In some embodiments, regions located in column 440 include a first chemical or biochemical compound at a first amount, regions located in column 442 include the first chemical or biochemical compound at a second amount that is distinct from the first amount, regions located in column 444 include the first chemical or biochemical compound at a third amount that is distinct from the first amount and the second amount, and regions located in column 446 include the first chemical or biochemical compound at a fourth amount that is distinct from the first amount, the second amount, and the third amount. In addition, regions located in row 450 include a second chemical or biochemical compound at a fifth amount, regions located in row 452 include the second chemical or biochemical compound at a sixth amount that is distinct from the fifth amount, regions located in row 454 include the second chemical or biochemical compound at a seventh amount that is distinct from the fifth amount and the sixth amount, and regions located in row 456 include the second chemical or biochemical compound at an eighth amount that is distinct from the fifth amount, the sixth amount, and the seventh amount.

Although FIG. 4B illustrates an example with a 4-by-4 array of regions, a person having ordinary skill in the art would understand that a smaller array (e.g., 3-by-3 array) or a larger array (e.g., 12-by-8 array or 24-by-16 array) can be configured in analogous manners.

Figure 4C:
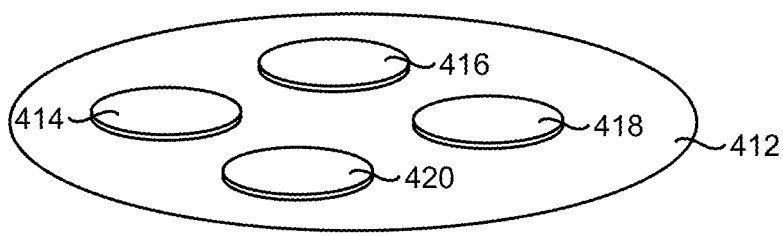
FIG. 4C is a perspective view of a first example configuration of chemical and/or biochemical compounds disposed on a respective region in accordance with some embodiments.

FIG. 4C illustrates a first example configuration of chemical and/or biochemical compounds disposed on a respective region in accordance with some embodiments. As shown in FIG. 4C, in some embodiments, the chemical and/or biochemical compounds are dispersed over the respective region. In some embodiments, the chemical and/or biochemical compounds do not overlap with one another, as shown in FIG. 4C. For example chemical and/or biochemical compounds 414, 416, 418, and 420 are dispersed on sheet 412 and do not overlap with one another in FIG. 4C.

Figure 4D:
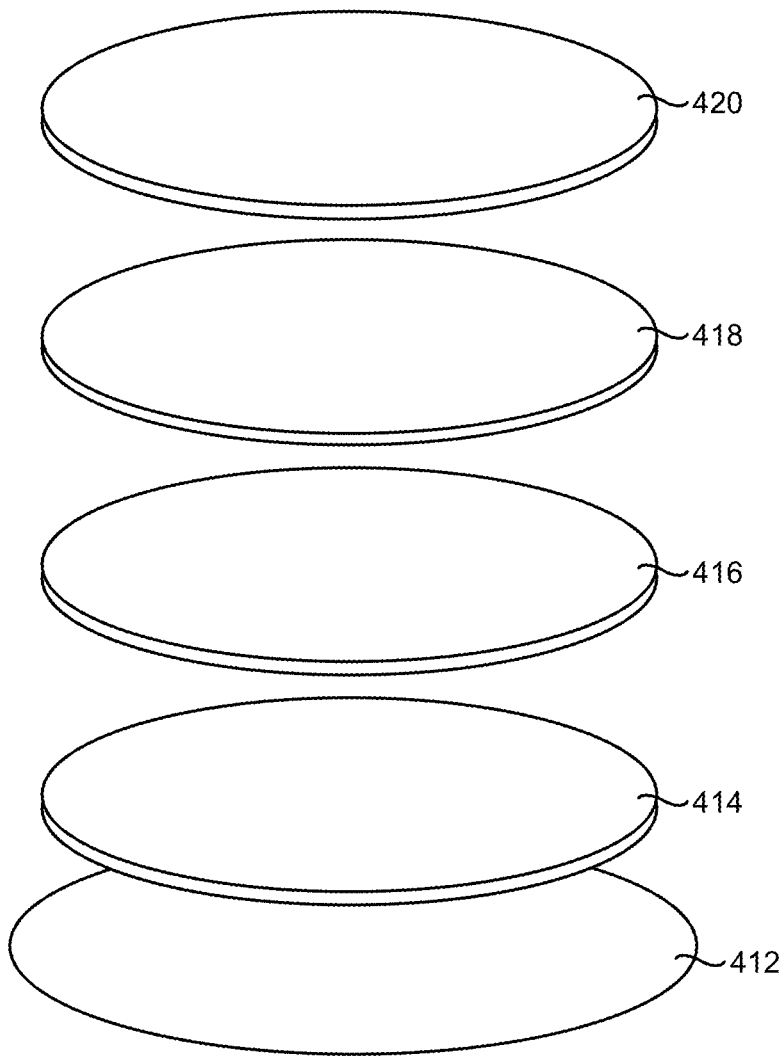
FIG. 4D is an exploded view of a second example configuration of chemical and/or biochemical compounds disposed on a respective region in accordance with some embodiments.

FIG. 4D is an exploded view illustrating a second example configuration of chemical and/or biochemical compounds disposed on a respective region in accordance with some embodiments. In FIG. 4D, each chemical and/or biochemical compound forms a layer. For example, chemical or biochemical compound 414 forms a first layer, chemical or biochemical compound 416 forms a second layer, chemical or biochemical compound 418 forms a third layer, and chemical or biochemical compound 420 forms a fourth layer. In FIG. 4D, the first layer of chemical or biochemical compound 414 is located over sheet 412, the second layer of chemical or biochemical compound 416 is located over the second layer of chemical or biochemical compound 414, the third layer of chemical or biochemical compound 418 is located over the third layer of chemical or biochemical compound 416, and the fourth layer of chemical or biochemical compound 420 is located over the third layer of chemical or biochemical compound 418.

In some embodiments, the first layer of chemical or biochemical compound 414 is located on sheet 412 (e.g., the first layer of chemical or biochemical compound 420 is in direct contact with sheet 412), the second layer of chemical or biochemical compound 416 is located on the first layer of chemical or biochemical compound 414 (e.g., the second layer of chemical or biochemical compound 416 is in direct contact with the first layer of chemical or biochemical compound 414), the third layer of chemical or biochemical compound 418 is located on the second layer of chemical or biochemical compound 416 (e.g., the third layer of chemical or biochemical compound 418 is in direct contact with the second layer of chemical or biochemical compound 416), and/or the fourth layer of chemical or biochemical compound 420 is located on the third layer of chemical or biochemical compound 418 (e.g., the fourth layer of chemical or biochemical compound 420 is in direct contact with the third layer of chemical or biochemical compound 418).

Although FIGS. 4C and 4D illustrate two example configurations, a person having ordinary skill in the art would understand that the chemical and/or biochemical compounds can be disposed in other configurations. For example, another configuration may include a first layer of chemical or biochemical compound 414 and three chemical and/or biochemical compounds 416, 418, and 420 disposed on the first layer of chemical or biochemical compound 414 (e.g., each of three chemical and/or biochemical compounds 416, 418, and 420 is in direct contact with the first layer of chemical or biochemical compound 414). In yet another configuration, the first layer of chemical or biochemical compound 414 may be disposed over or between the three chemical and/or biochemical compounds 416, 418, and 420 (e.g., chemical and/or biochemical compounds 416 and 418 are located below the first layer of chemical or biochemical compound 414 and chemical or biochemical compound 420 is located above the first layer of chemical or biochemical compound 414).

Figure 4E:
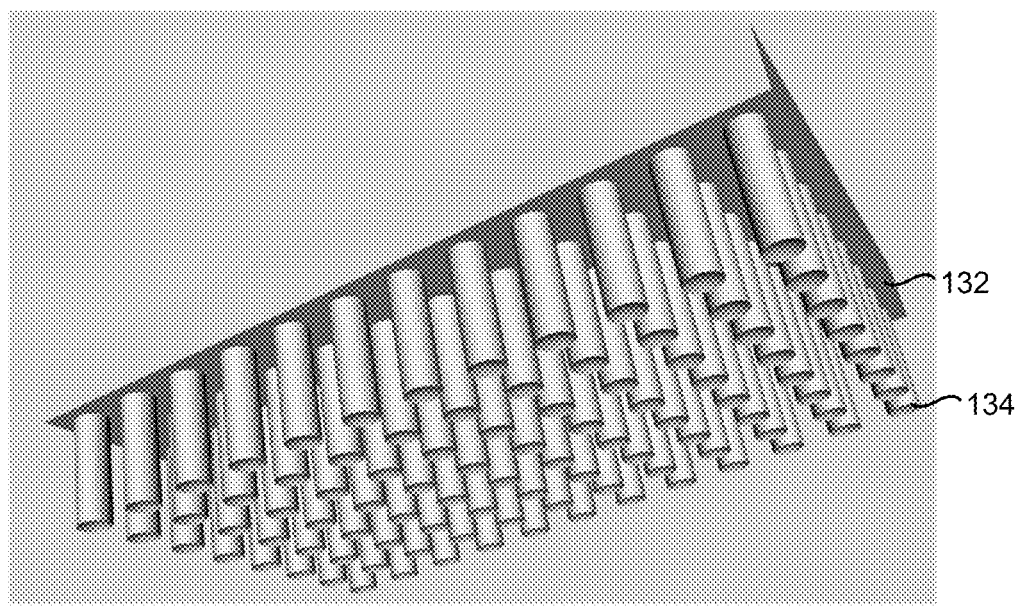
FIG. 4E illustrates an example loading device in accordance with some embodiments.

FIG. 4E illustrates example loading device 132 in accordance with some embodiments. Loading device 132 (e.g., a punch device) in FIG. 4E includes a plurality of release components 134 (e.g., pillars, rods, tubes, etc.). In some embodiments, each release component 134 includes one or more blades to release portions of the sheet.

Figure 4F:
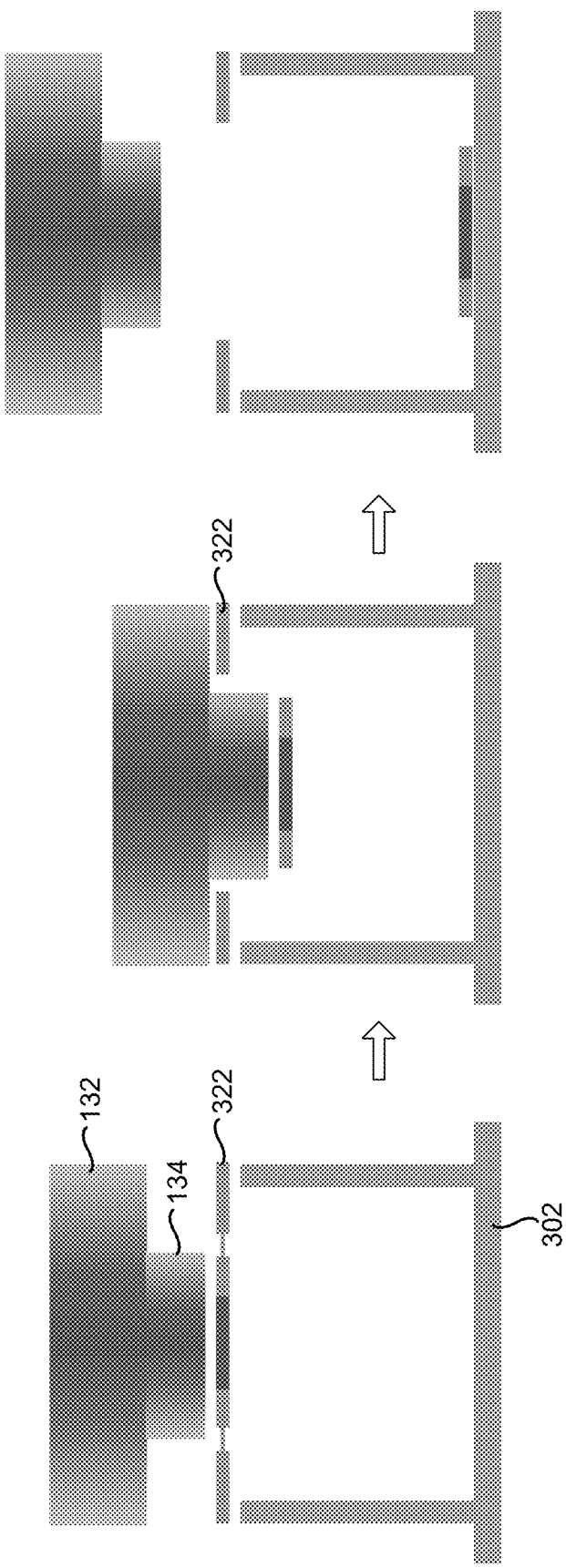
FIG. 4F illustrates operations for releasing one or more portions of a sheet with a loading device in accordance with some embodiments.

FIG. 4F illustrates operations for releasing one or more portions of sheet 322 with a loading device in accordance with some embodiments.

In FIG. 4F, sheet 322 is positioned above well plate 302. In some embodiments, a first portion of sheet 322 is aligned with a well of well plate 302. Loading device 132 is positioned above sheet 322, where release component 134 is aligned with the first portion of sheet 322. Loading device 132 and release component 134 are pressed on sheet 322, and release component 134 causes the first portion of sheet 322 to be removed from the rest of sheet 322. The removed (or released) first portion of sheet 322 falls into the well of well plate 302.

Figure 5A:
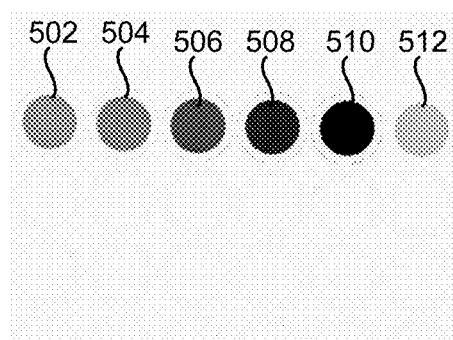
FIG. 5A illustrates a fluorescent image of wells with different numbers of cells in accordance with some embodiments.

FIG. 5A illustrates a fluorescent image of wells with different numbers of cells remaining therein in accordance with some embodiments. Cells remaining in wells of the well plate (e.g., after incubation) can be quantified using various methods, such as spectrophotometry, fluorescence measurements, camera imaging, etc. In some embodiments, the cells remaining in the wells of the well plate are exposed to one or more reagents for the quantification (e.g., the one or more reagents, such as the alamarBlue reagent, are added to the cells remaining in the wells of the well plate).

Figure 5B:
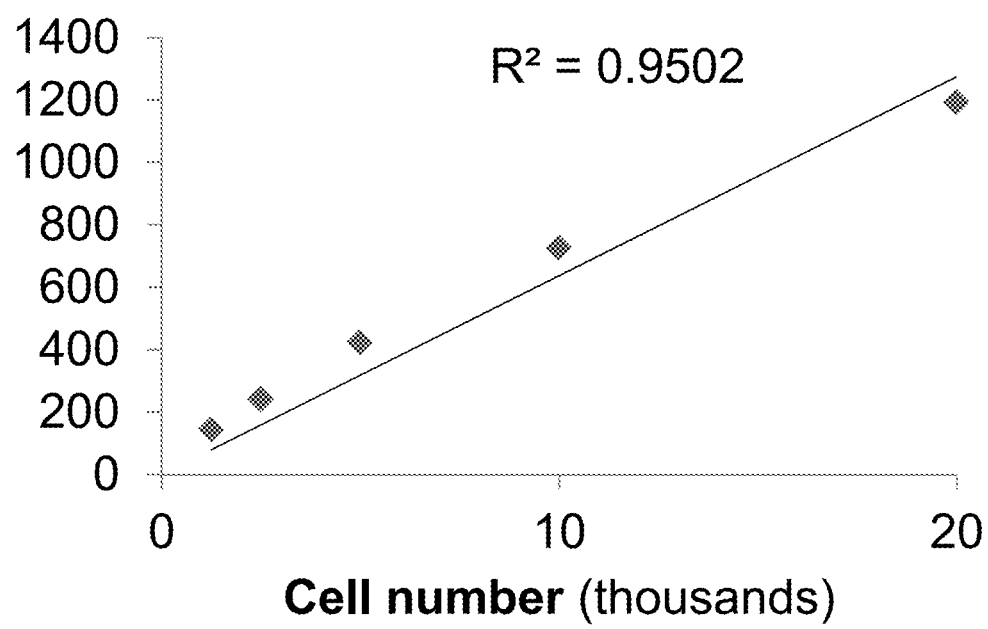
FIG. 5B shows fluorescence intensities measured from the wells shown in FIG. 5A.

FIG. 5B shows fluorescence intensities measured from the wells shown in FIG. 5A. The chart depicted in FIG. 5B shows that the fluorescence intensity is substantially proportional to the number of cells remaining in each well.

In light of these principles, we now turn to certain embodiments.

In accordance with some embodiments, an article of manufacture (e.g., a sheet, such as paper or film, or a well plate, such as a 96 well plate or a 384 well plate) includes an array of distinct and separate regions with respective chemical and/or biochemical compounds (e.g., pharmaceutical compounds) located thereon (e.g., regions 402, 404, 406, and 408 in FIG. 4A). The array of distinct and separate regions includes a first region with a first set of one or more chemical and/or biochemical compounds located thereon (e.g., region 402); a second region, that is distinct and separate from the first region, with a second set of one or more chemical and/or biochemical compounds, that is distinct from the first set of one or more chemical and/or biochemical compounds, located thereon (e.g., region 404); and a third region, that is distinct and separate from the first region and the second region, with a third set of one or more chemical and/or biochemical compounds, that is distinct from the first set of one or more chemical and/or biochemical compounds and the second set of one or more chemical and/or biochemical compounds, located thereon (e.g., region 406).

In some embodiments, a respective set of one or more chemical and/or biochemical compounds is printed, sprayed, brushed, dropped, soaked, coated on a corresponding region.

In some embodiments, respective regions of the array of distinct and separate regions include two or more layers of chemical and/or biochemical compounds (e.g., FIG. 4D). For example, in some embodiments, the first set of one or more chemical and/or biochemical compounds includes a first layer of one or more chemical and/or biochemical compounds (e.g., layer 414) and a second layer of one or more chemical and/or biochemical compounds located on the first layer (e.g., layer 416). In some embodiments, respective regions of the array of distinct and separate regions include three or more layers of chemical and/or biochemical compounds (e.g., layers 414, 416, and 418).

In some embodiments, the array of distinct and separate regions includes a fourth region, that is distinct and separate from the first region, the second region, and the third region, with a fourth set of one or more chemical and/or biochemical compounds, that is distinct from the first set of one or more chemical and/or biochemical compounds, the second set of one or more chemical and/or biochemical compounds, and the third set of one or more chemical and/or biochemical compounds, located thereon (e.g., region 408 in FIG. 4A).

In some embodiments, the article of manufacture further includes one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located (e.g., region 430 in FIG. 4A).

In some embodiments, the first region and the second region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The first region and the third region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The first region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The second region and the third region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The second region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. The third region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located. For example, in some embodiments, as shown in FIG. 1, the one or more chemical and/or biochemical compounds are located on central regions only (e.g., no chemical or biochemical compound is located on regions between any two adjacent central regions). In some embodiments, one or more chemical and/or biochemical compounds are located on a region between any two adjacent central regions, but the one or more chemical and/or biochemical compounds located on the region between any two adjacent central regions are not part of the first set of one or more chemical and/or biochemical compounds, the second set of one or more chemical and/or biochemical compounds, the third set of one or more chemical and/or biochemical compounds, or the fourth set of one or more chemical and/or biochemical compounds. In some embodiments, one or more chemical and/or biochemical compounds are located on a region between any two adjacent central regions, but the one or more chemical and/or biochemical compounds located on the region between any two adjacent central regions are independent of the first set of one or more chemical and/or biochemical compounds, the second set of one or more chemical and/or biochemical compounds, the third set of one or more chemical and/or biochemical compounds, or the fourth set of one or more chemical and/or biochemical compounds (e.g., the first set of one or more chemical and/or biochemical compounds may or may not include the one or more chemical and/or biochemical compounds located on the region between any two adjacent central regions).

In some embodiments, the article of manufacture further includes a well plate defining an array of distinct wells (e.g., well plate 122 in FIG. 1). A respective well of the array of distinct wells includes a respective region of the array of distinct and separate regions (e.g., FIG. 3A).

In some embodiments, the article of manufacture includes an insert (e.g., insert 312, FIG. 3B) having an array of dippers that are positioned to correspond to an array of distinct wells of a well plate, a respective dipper (e.g., dipper 318, FIG. 3B) of the array of dippers including a respective region of the array of distinct and separate regions.

In some embodiments, the respective dipper includes a permeable membrane (e.g., permeable membrane 316, FIG. 3B) with a respective set of one or more chemical and/or biochemical compounds located thereon (e.g., chemical and/or biochemical compounds 314, FIG. 3B).

In some embodiments, the article of manufacture further includes a sheet with the array of distinct and separate regions with respective compounds located thereon (e.g., a sheet of a film or paper as shown in FIG. 2B).

In some embodiments, the article of manufacture is the sheet with the array of distinct and separate regions with respective compounds located thereon.

In some embodiments, the sheet is at least partially water-soluble (e.g., the sheet includes a film that is made of a water-soluble material).

In some embodiments, the sheet is not water-soluble (e.g., a transparent plastic film that is not water-soluble). In some embodiments, the sheet is soluble in a solvent that is not water. In some embodiments, the sheet is biocompatible (e.g., the sheet is not harmful to live cells). As used herein, a biocompatible object refers to an object that is not harmful to live cells.

In some embodiments, the sheet defines, for a respective region of the array of distinct and separate regions, one or more through holes so that the respective region is connected to a rest of the sheet by one or more connecting regions (e.g., in FIG. 1, three holes 108 are defined so that central region 104 is connected to the rest of sheet 102 by three bridges 106 or bridging regions).

In some embodiments, each of the one or more connecting regions has a shape of a spoke connecting the respective region to the rest of the sheet, the one or more connecting regions arranged around the respective region. For example, as shown in FIG. 1, in some embodiments, central region 104 and bridges 106 have a shape of a hub and spokes, where central region 104 corresponds to the hub and bridges 106 correspond to spokes radially arranged around central region 104.

In some embodiments, the first set of one or more chemical and/or biochemical compounds, the second set of one or more chemical and/or biochemical compounds, and the third set of one or more chemical and/or biochemical compounds include one or more chemical and/or biochemical compounds selected from a group consisting of (i) one or more cancer drugs (e.g., doxorubicin) and (ii) one or more antibiotics (e.g., carbapenem).

In some embodiments, the first set of one or more chemical and/or biochemical compounds, the second set of one or more chemical and/or biochemical compounds, and the third set of one or more chemical and/or biochemical compounds include either one or more cancer drugs or one or more antibiotics. For example, in some embodiments, the first set of one or more chemical and/or biochemical compounds, the second set of one or more chemical and/or biochemical compounds, and the third set of one or more chemical and/or biochemical compounds include one or more cancer drugs and no antibiotics. In another example, the first set of one or more chemical and/or biochemical compounds, the second set of one or more chemical and/or biochemical compounds, and the third set of one or more chemical and/or biochemical compounds include one or more antibiotics and no cancer drugs.

In some embodiments, the first set of one or more chemical and/or biochemical compounds includes one or more water-soluble compounds. The second set of one or more chemical and/or biochemical compounds includes one or more water-soluble compounds. The third set of one or more chemical and/or biochemical compounds includes one or more water-soluble compounds. In some embodiments, the first set of one or more chemical and/or biochemical compounds, the second set of one or more chemical and/or biochemical compounds, and the third set of one or more chemical and/or biochemical compounds all include a common compound that is water-soluble. In some embodiments, the first set of one or more chemical and/or biochemical compounds, the second set of one or more chemical and/or biochemical compounds, and the third set of one or more chemical and/or biochemical compounds are all water-soluble compounds.

In some embodiments, the first set of one or more chemical and/or biochemical compounds includes one or more chemical and/or biochemical compounds that are soluble to a solvent that is not water. The second set of one or more chemical and/or biochemical compounds includes one or more chemical and/or biochemical compounds that are soluble to the solvent that is not water. The third set of one or more chemical and/or biochemical compounds includes one or more chemical and/or biochemical compounds that are soluble to a solvent that is not water. In some embodiments, the first set of one or more chemical and/or biochemical compounds, the second set of one or more chemical and/or biochemical compounds, and the third set of one or more chemical and/or biochemical compounds all include a common compound that is soluble to a solvent that is not water. In some embodiments, the first set of one or more chemical and/or biochemical compounds, the second set of one or more chemical and/or biochemical compounds, and the third set of one or more chemical and/or biochemical compounds are all compounds that are soluble to a solvent that is not water.

In some embodiments, the first compound is a cancer drug (e.g., doxorubicin) or an antibiotic (e.g., carbapenem).

In some embodiments, the first set of one or more chemical and/or biochemical compounds includes a second compound at a fourth amount. The second set of one or more chemical and/or biochemical compounds includes the second compound at a fifth amount that is distinct from the fourth amount. The third set of one or more chemical and/or biochemical compounds includes the second compound at a sixth amount that is distinct from the fourth amount and the fifth amount (e.g., FIG. 4B).

In some embodiments, the first set of one or more chemical and/or biochemical compounds includes a second compound at the fourth amount. The second set of one or more chemical and/or biochemical compounds includes the second compound at the fourth amount. The third set of one or more chemical and/or biochemical compounds includes the second compound at the fourth amount (e.g., FIG. 4B).

In some embodiments, the second compound is a cancer drug (e.g., methotrexate) or an antibiotic (e.g., tigecycline); and the second compound is distinct from the first compound. In some embodiments, the first compound is a first cancer drug (e.g., doxorubicin) and the second compound is a second cancer drug (e.g., methotrexate) that is distinct from the first cancer drug. In some embodiments, the first compound is a first antibiotic (e.g., carbapenem) and the second compound is a second antibiotic (e.g., tigecycline) that is distinct from the first antibiotic.

In some embodiments, the first set of one or more chemical and/or biochemical compounds includes a first amount of a first compound, the second set of one or more chemical and/or biochemical compounds includes a second amount of the first compound, and the third set of one or more chemical and/or biochemical compounds includes a third amount of the first compound (e.g., FIG. 4B). The second amount is distinct from the first amount. The third amount is distinct from the first amount and the second amount.

In some embodiments, the first set of one or more chemical and/or biochemical compounds includes a fourth amount of a second compound, the second set of one or more chemical and/or biochemical compounds includes a fifth amount of the second compound, and the third set of one or more chemical and/or biochemical compounds includes a sixth amount of the second compound (e.g., FIG. 4B). The fifth amount is distinct from the fourth amount. The sixth amount is distinct from the fourth amount and the fifth amount.

In some embodiments, the first set of one or more chemical and/or biochemical compounds includes a particular release control reagent. The second set of one or more chemical and/or biochemical compounds includes the particular release control reagent. The third set of one or more chemical and/or biochemical compounds includes the particular release control reagent. In some embodiments, the particular release control reagent is configured to control the release speed of one or more chemical and/or biochemical compounds in the first set of one or more chemical and/or biochemical compounds, the second set of one or more chemical and/or biochemical compounds, and the third set of one or more chemical and/or biochemical compounds. In some embodiments, the particular release control reagent chemically and/or physically slows the release of the one or more chemical and/or biochemical compounds. In some embodiments, the particular release control reagent includes gelatine. In some embodiments, a respective set of one or more chemical and/or biochemical compounds includes three or more layers of the one or more chemical and/or biochemical compounds and multiple layers of the particular release control reagent located between any two adjacent layers of the one or more chemical and/or biochemical compounds.

In some embodiments, the first set of one or more chemical and/or biochemical compounds includes a seventh amount of the particular release control reagent. The second set of one or more chemical and/or biochemical compounds includes the seventh amount of the particular release control reagent. The third set of one or more chemical and/or biochemical compounds includes the seventh amount of the particular release control reagent. For example, the first set of one or more chemical and/or biochemical compounds, the second set of one or more chemical and/or biochemical compounds, and the third set of one or more chemical and/or biochemical compounds include a same amount of the particular release control reagent.

In some embodiments, the first set of one or more chemical and/or biochemical compounds includes a seventh amount of the particular release control reagent. The second set of one or more chemical and/or biochemical compounds includes an eighth amount of the particular release control reagent, the eighth amount being distinct from the seventh amount. The third set of one or more chemical and/or biochemical compounds includes a ninth amount of the particular release control reagent, the ninth amount being distinct from the seventh amount and the eighth amount. For example, the first set of one or more chemical and/or biochemical compounds, the second set of one or more chemical and/or biochemical compounds, and the third set of one or more chemical and/or biochemical compounds include different amounts of the particular release control reagent.

In some embodiments, the first set of one or more chemical and/or biochemical compounds includes a particular growth control reagent. The second set of one or more chemical and/or biochemical compounds includes the particular growth control reagent. The third set of one or more chemical and/or biochemical compounds includes the particular growth control reagent. As used herein, a growth control reagent refers to a reagent that is configured to enhance or suppress growth of a cell. For example, growth control reagents include growth enhance reagents (e.g., sugar, amino acids, buffering salts, etc.) and/or growth suppression reagents (e.g., anti-bacterial reagents or bacterial inhibitors to reduce or prevent growth of bacteria in case of a respective set of one or more chemical and/or biochemical compounds including cancer drugs). Growth enhance reagents are used to maintain or enhance the viability of cells during incubation.

In some embodiments, the first set of one or more chemical and/or biochemical compounds includes a tenth amount of the particular growth control reagent. The second set of one or more chemical and/or biochemical compounds includes the tenth amount of the particular growth control reagent. The third set of one or more chemical and/or biochemical compounds includes the tenth amount of the particular growth control reagent. For example, the first set of one or more chemical and/or biochemical compounds, the second set of one or more chemical and/or biochemical compounds, and the third set of one or more chemical and/or biochemical compounds include a same amount of the particular growth control reagent.

In some embodiments, the first set of one or more chemical and/or biochemical compounds includes a tenth amount of the particular growth control reagent. The second set of one or more chemical and/or biochemical compounds includes an eleventh amount of the particular growth control reagent. The eleventh amount is distinct from the tenth amount. The third set of one or more chemical and/or biochemical compounds includes a twelfth amount of the particular growth control reagent. The twelfth amount is distinct from the tenth amount and the eleventh amount. For example, the first set of one or more chemical and/or biochemical compounds, the second set of one or more chemical and/or biochemical compounds, and the third set of one or more chemical and/or biochemical compounds include different amounts of the particular growth control reagent.

In accordance with some embodiments, a method includes obtaining any sheet described herein. The method also includes obtaining a well plate defining an array of distinct wells, the array of distinct wells including a first well, a second well that is distinct from the first well, and a third well that is distinct from the first well and the second well; removing, from the sheet, the first region of the sheet and dispensing the first region of the sheet into the first well; removing, from the sheet, the second region of the sheet and dispensing the second region of the sheet into the second well; and removing, from the sheet, the third region of the sheet and dispensing the third region of the sheet into the third well (e.g., FIG. 4F).

In some embodiments, the first region of the sheet, the second region of the sheet, and the third region of the sheet are concurrently removed and dispensed into respective wells. For example, loading device 132 shown in FIG. 4E includes a plurality of release components 134, which are used to concurrently remove a plurality of regions of the sheet (e.g., a film).

In accordance with some embodiments, a method includes obtaining any well plate described herein.

In some embodiments, the method further includes providing a first portion of a sample (e.g., cells) in the first well; providing a second portion of the sample in the second well; and providing a third portion of the sample in the third well. In some embodiments, the sample includes cancer cells (e.g., a first portion of cancer cells is placed in the first well, a second portion of cancer cells is placed in the second well, and a third portion of cancer cells is placed in the third well). In some embodiments, the sample includes infected cells (e.g., cells infected with virus, bacteria, etc.). In some embodiments, the sample includes infectious or infecting cells (e.g., bacteria).

In some embodiments, the method further includes incubating the first portion of the sample in the first well; incubating the second portion of the sample in the second well; and incubating the third portion of the sample in the third well.

In some embodiments, the method further includes determining an amount of the sample in the first well; determining an amount of the sample in the second well; and determining an amount of the sample in the third well. In some embodiments, the amount of the sample remaining in each well is used to identify one or more concentrations or amounts of chemical and/or biochemical compounds that provide a desired performance (e.g., the vitality of cancer cells or infecting cells below a predefined threshold or the vitality of infected cells or non-cancer cells above a predefined threshold).

In some embodiments, the method further includes selecting a particular set of one or more chemical and/or biochemical compounds based on the amount of the sample in the first well, the amount of the sample in the second well, and the amount of the sample in the third well.

In some embodiments, a particular set of one or more chemical and/or biochemical compounds that corresponds to a large amount of the sample in a well is selected (e.g., the particular set of one or more chemical and/or biochemical compounds, such as antiviral and/or antibacterial compounds, has increased the viability of cells). In some embodiments, a particular set of one or more chemical and/or biochemical compounds that corresponds to a small amount of the sample in a well is selected (e.g., the particular set of one or more chemical and/or biochemical compounds, such as anti-cancer compounds, has reduced the viability of cancer cells). In another example, anti-bacterial compounds have reduced the viability of infectious cells (e.g., bacteria).

In some embodiments, the method further includes treating a patient with one or more chemical and/or biochemical compounds based on selection of the particular set of one or more chemical and/or biochemical compounds. For example, once a particular set of one or more chemical and/or biochemical compounds is selected, the particular set of one or more chemical and/or biochemical compounds is used for treating the patient.

In some embodiments, the method further includes selecting a composition of one or more chemical and/or biochemical compounds for treating a patient based on selection of the particular set of one or more chemical and/or biochemical compounds. For example, when the particular set of one or more chemical and/or biochemical compounds includes a first amount of a first chemical compound and a second amount of a second chemical compound, where the second amount is twice the first amount, a third amount of the first chemical compound and a fourth amount of the second chemical compound are selected for treating the patient, where the fourth amount is twice the third amount so that the ratio between the first compound and the second compound remain the same.

In accordance with some embodiments, a punching device (e.g., a loading device) for dispensing a plurality of respective regions of a sheet into respective wells of a well plate includes a frame defining a reference plane; and a plurality of pillars mounted on the frame. A respective pillar of the plurality of pillars is mounted substantially perpendicular to the reference plane. For example, loading device 132 shown in FIG. 4E includes a frame defining a reference plane and a plurality of pillars 134 mounted substantially perpendicular to the reference plane. In some embodiments, the plurality of pillars 134 is deemed to be mounted substantially perpendicular to the reference plane when a representative angle between the plurality of pillars 134 and the reference plane is between 70° and 110°. In some embodiments, the plurality of pillars 134 is deemed to be mounted substantially perpendicular to the reference plane when a representative angle between the plurality of pillars 134 and the reference plane is between 80° and 100°. In some embodiments, the plurality of pillars 134 is deemed to be mounted substantially perpendicular to the reference plane when a representative angle between the plurality of pillars 134 and the reference plane is between 85° and 95°.

In some embodiments, each pillar of the plurality of pillars is a cylindrical pillar (e.g., FIG. 4E)

In some embodiments, each pillar of the plurality of pillars is hollow at least in a portion that is located away from the frame. In some embodiments, each pillar of the plurality of pillars is entirely hollow (e.g., each pillar has a shape of a pipe). In some embodiments, each pillar of the plurality of pillars has a tip that has a shape of a pipe. In some embodiments, a portion of the pillar is not hollow.

In accordance with some embodiments, a method of processing an article of manufacture includes obtaining the article of manufacture, placing a first set of one or more chemical and/or biochemical compounds on a first region of the article of manufacture, placing a second set of one or more chemical and/or biochemical compounds, distinct from the first set of one or more chemical and/or biochemical compounds, on a second region of the article of manufacture that is distinct and separate from the first region, and placing a third set of one or more chemical and/or biochemical compounds, distinct from the first set of one or more chemical and/or biochemical compounds and the second set of one or more chemical and/or biochemical compounds, on a third region of the article of manufacture that is distinct and separate from the first region and the second region.

In some embodiments, placing the first set of one or more chemical and/or biochemical compounds on the first region of the article of manufacture includes printing at least a subset of the first set of one or more chemical and/or biochemical compounds on the first region of the article of manufacture, placing the second set of one or more chemical and/or biochemical compounds on the second region of the article of manufacture includes printing at least a subset of the second set of one or more chemical and/or biochemical compounds on the second region of the article of manufacture, and placing the third set of one or more chemical and/or biochemical compounds on the third region of the article of manufacture includes printing at least a subset of the third set of one or more chemical and/or biochemical compounds on the third region of the article of manufacture. In some embodiments, a respective printing is performed using an inkjet printer.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best use the invention and various described embodiments with various modifications as are suited to the particular use contemplated.

What is claimed is:

1. An article of manufacture, comprising:
    a sheet with an array of distinct and separate regions with respective chemical and/or biochemical compounds located thereon, the array of distinct and separate regions including:
        a first region with a first set of one or more chemical and/or biochemical compounds located thereon, wherein the first set of one or more chemical and/or biochemical compounds includes a particular compound;
        a second region, that is distinct and separate from the first region, with a second set of one or more chemical and/or biochemical compounds, that is distinct from the first set of one or more chemical and/or biochemical compounds, located thereon, wherein the second set of one or more chemical and/or biochemical compounds does not include the particular compound; and
        a third region, that is distinct and separate from the first region and the second region, with a third set of one or more chemical and/or biochemical compounds, that is distinct from the first set of one or more chemical and/or biochemical compounds and the second set of one or more chemical and/or biochemical compounds, located thereon,
    wherein:
        the sheet defines, for a respective region of the array of distinct and separate regions, one or more through-holes extending from one planar side of the sheet to an opposite planar side of the sheet and one or more connecting regions adjacent to the one or more through-holes so that the respective region is connected to a rest of the sheet by the one or more connecting regions; and
        each of the one or more connecting regions has a shape of a spoke connecting the respective region to the rest of the sheet, the one or more connecting regions arranged around the respective region.

2. The article of manufacture of claim 1, wherein:
    the array of distinct and separate regions includes a fourth region, that is distinct and separate from the first region, the second region, and the third region, with a fourth set of one or more chemical and/or biochemical compounds, that is distinct from the first set of one or more chemical and/or biochemical compounds, the second set of one or more chemical and/or biochemical compounds, and the third set of one or more chemical and/or biochemical compounds, located thereon.

3. The article of manufacture of claim 2, further comprising:
    one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located.

4. The article of manufacture of claim 3, wherein:
    the first region and the second region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located;

the first region and the third region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located;

the first region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located;

the second region and the third region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located;

the second region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located; and the third region and the fourth region are separated by at least a region of the one or more regions, on which none of the first set of one or more chemical and/or biochemical compounds, the second set of one or more chemical and/or biochemical compounds, the third set of one or more chemical and/or biochemical compounds, and the fourth set of one or more chemical and/or biochemical compounds is located.

5. The article of manufacture of claim 1, further comprising:
a well plate defining an array of distinct wells, a respective well of the array of distinct wells aligned with a respective region of the array of distinct and separate regions of the sheet.

6. The article of manufacture of claim 1, comprising:
an insert having an array of dippers that are positioned to correspond to an array of distinct wells of a well plate, a respective dipper of the array of dippers including a respective region of the array of distinct and separate regions, wherein the respective dipper holds the respective region of the array of distinct and separate regions by one or more lateral outer edges of the respective region of the array of distinct and separate regions.

7. The article of manufacture of claim 6, wherein the respective dipper includes a permeable membrane with a respective set of one or more chemical and/or biochemical compounds located thereon.

8. The article of manufacture of claim 1, wherein:
the article of manufacture is the sheet with the array of distinct and separate regions with respective compounds located thereon.

9. The article of manufacture of claim 1, wherein:
the sheet is at least partially water-soluble.

10. The article of manufacture of claim 1, wherein:
the first set of one or more chemical and/or biochemical compounds, the second set of one or more chemical and/or biochemical compounds, and the third set of one or more chemical and/or biochemical compounds include one or more chemical and/or biochemical compounds selected from a group consisting of (i) one or more cancer drugs and (ii) one or more antibiotics.

11. The article of manufacture of claim 10, wherein:
the first set of one or more chemical and/or biochemical compounds, the second set of one or more chemical and/or biochemical compounds, and the third set of one or more chemical and/or biochemical compounds include either one or more cancer drugs or one or more antibiotics.

12. The article of manufacture of claim 1, wherein:
the first set of one or more chemical and/or biochemical compounds includes one or more water-soluble compounds;
the second set of one or more chemical and/or biochemical compounds includes one or more water-soluble compounds; and
the third set of one or more chemical and/or biochemical compounds includes one or more water-soluble compounds.

13. The article of manufacture of claim 1, wherein:
the first set of one or more chemical and/or biochemical compounds includes one or more chemical and/or biochemical compounds that are soluble to a solvent that is not water;
the second set of one or more chemical and/or biochemical compounds includes one or more chemical and/or biochemical compounds that are soluble to the solvent that is not water; and
the third set of one or more chemical and/or biochemical compounds includes one or more chemical and/or biochemical compounds that are soluble to a solvent that is not water.

14. The article of manufacture of claim 1, wherein:
the first set of one or more chemical and/or biochemical compounds includes a first compound at a first amount;
the second set of one or more chemical and/or biochemical compounds includes the first compound at a second amount that is distinct from the first amount; and
the third set of one or more chemical and/or biochemical compounds includes the first compound at a third amount that is distinct from the first amount and the second amount.

15. The article of manufacture of claim 14, wherein:
the first compound is a cancer drug or an antibiotic.

16. The article of manufacture of claim 14, wherein:
the first set of one or more chemical and/or biochemical compounds includes a second compound at a fourth amount;
the second set of one or more chemical and/or biochemical compounds includes the second compound at a fifth amount that is distinct from the fourth amount; and
the third set of one or more chemical and/or biochemical compounds includes the second compound at a sixth amount that is distinct from the fourth amount and the fifth amount.

17. The article of manufacture of claim 16, wherein:
the second compound is a cancer drug or an antibiotic; and
the second compound is distinct from the first compound.

18. The article of manufacture of claim 14, wherein:
the first set of one or more chemical and/or biochemical compounds includes a fourth amount of a second compound;
the second set of one or more chemical and/or biochemical compounds includes a fifth amount of the second compound, the fifth amount being distinct from the fourth amount; and
the third set of one or more chemical and/or biochemical compounds includes a sixth amount of the second compound, the sixth amount being distinct from the fourth amount and the fifth amount.

19. The article of manufacture of claim 1, wherein:
the first set of one or more chemical and/or biochemical compounds includes a particular release control reagent;
the second set of one or more chemical and/or biochemical compounds includes the particular release control reagent; and
the third set of one or more chemical and/or biochemical compounds includes the particular release control reagent.

20. The article of manufacture of claim 19, wherein:
the first set of one or more chemical and/or biochemical compounds includes a seventh amount of the particular release control reagent;
the second set of one or more chemical and/or biochemical compounds includes the seventh amount of the particular release control reagent; and
the third set of one or more chemical and/or biochemical compounds includes the seventh amount of the particular release control reagent.

21. The article of manufacture of claim 19, wherein:
the first set of one or more chemical and/or biochemical compounds includes a seventh amount of the particular release control reagent;
the second set of one or more chemical and/or biochemical compounds includes an eighth amount of the particular release control reagent, the eighth amount being distinct from the seventh amount; and
the third set of one or more chemical and/or biochemical compounds includes a ninth amount of the particular release control reagent, the ninth amount being distinct from the seventh amount and the eighth amount.

22. The article of manufacture of claim 19, wherein:
the first set of one or more chemical and/or biochemical compounds includes a particular growth control reagent;
the second set of one or more chemical and/or biochemical compounds includes the particular growth control reagent; and
the third set of one or more chemical and/or biochemical compounds includes the particular growth control reagent.

23. The article of manufacture of claim 22, wherein:
the first set of one or more chemical and/or biochemical compounds includes a tenth amount of the particular growth control reagent;
the second set of one or more chemical and/or biochemical compounds includes the tenth amount of the particular growth control reagent; and
the third set of one or more chemical and/or biochemical compounds includes the tenth amount of the particular growth control reagent.

24. The article of manufacture of claim 22, wherein:
the first set of one or more chemical and/or biochemical compounds includes a tenth amount of the particular growth control reagent;
the second set of one or more chemical and/or biochemical compounds includes an eleventh amount of the particular growth control reagent, the eleventh amount being distinct from the tenth amount; and
the third set of one or more chemical and/or biochemical compounds includes a twelfth amount of the particular growth control reagent, the twelfth amount being distinct from the tenth amount and the eleventh amount.

25. The article of manufacture of claim 1, wherein:
the first set of one or more chemical and/or biochemical compounds is soluble in a solvent.

26. The article of manufacture of claim 25, wherein:
the second set of one or more chemical and/or biochemical compounds is soluble in the solvent.

27. The article of manufacture of claim 26, wherein:
the third set of one or more chemical and/or biochemical compounds is soluble in the solvent.

28. The article of manufacture of claim 16, wherein:
the first compound is a first cancer drug; and
the second compound is a second cancer drug distinct from the first cancer drug.

29. The article of manufacture of claim 1, wherein:
the sheet defines three or more through-holes and three or more connecting regions so that the respective region is connected to the rest of the sheet by the three or more connecting regions.

30. The article of manufacture of claim 1, wherein:
the respective region is connected to the rest of the sheet only by the one or more connecting regions so that breaking the one or more connecting regions separates the respective region from the rest of the sheet.

* * * * *